(12) United States Patent
Saviola

(10) Patent No.: US 11,723,800 B2
(45) Date of Patent: Aug. 15, 2023

(54) EYEDROPPER BOTTLE HOLDER

(71) Applicant: James F. Saviola, Olney, MD (US)

(72) Inventor: James F. Saviola, Olney, MD (US)

( * ) Notice: Subject to any disclaimer, the term of this patent is extended or adjusted under 35 U.S.C. 154(b) by 378 days.

(21) Appl. No.: 17/224,311

(22) Filed: Apr. 7, 2021

(65) Prior Publication Data

US 2021/0220174 A1 Jul. 22, 2021

Related U.S. Application Data

(63) Continuation-in-part of application No. 16/546,589, filed on Aug. 21, 2019, now Pat. No. 10,993,836, which is a continuation-in-part of application No. 15/151,579, filed on May 11, 2016, now Pat. No. 10,426,660.

(51) Int. Cl.
*A61F 9/00* (2006.01)

(52) U.S. Cl.
CPC .................. *A61F 9/0026* (2013.01)

(58) Field of Classification Search
CPC ......... A61F 9/0026; A61H 35/02; B65D 1/08; B65D 47/18; B65D 47/185
See application file for complete search history.

(56) References Cited

U.S. PATENT DOCUMENTS

| | | | |
|---|---|---|---|
| 3,058,466 A | 10/1962 | Routson | |
| 3,872,866 A | 3/1975 | Lelicoff | |
| 3,924,621 A | 12/1975 | Cassimally | |
| 4,257,417 A | 3/1981 | Gibilisco | |
| 4,605,398 A | 8/1986 | Herrick | |
| 4,973,322 A | 11/1990 | Jewart | |
| 5,429,621 A | 7/1995 | Stahl | |
| 5,665,079 A * | 9/1997 | Stahl | A61F 9/0026 222/421 |
| 6,090,086 A * | 7/2000 | Bolden | A61F 9/0026 604/300 |
| D457,952 S | 5/2002 | Sherman | |
| D463,550 S | 9/2002 | Sherman | |
| D499,804 S | 12/2004 | Sherman | |
| 7,235,065 B1 | 6/2007 | Sorensen | |
| 10,426,660 B2 | 10/2019 | Saviola | |
| 2004/0267214 A1* | 12/2004 | Kerssies | A61F 9/0026 604/295 |
| 2005/0101921 A1* | 5/2005 | Sherman | A61F 9/0026 604/302 |
| 2019/0374382 A1 | 12/2019 | Saviola | |

FOREIGN PATENT DOCUMENTS

| | | |
|---|---|---|
| CA | 2908634 A1 | 10/2014 |
| JP | 11076366 A | 3/1999 |
| JP | 2003319999 A | 11/2003 |
| JP | 2007175374 A | 7/2007 |
| JP | 2011152380 A | 8/2011 |

* cited by examiner

*Primary Examiner* — Jessica Arble
(74) *Attorney, Agent, or Firm* — James G. Passe; Passe Intellectual Property, LLC

(57) ABSTRACT

The present invention is a device for holding an ophthalmic bottle of drops and instilling them in a patient's eye. The device rests on the boney lower orbital ridge for stability and correct delivery.

4 Claims, 6 Drawing Sheets

EYEDROPPER BOTTLE HOLDER

This application is a continuation-in-part of U.S. non-provisional application Ser. No. 16/546,589 filed on Aug. 21, 2019, which is a continuation-in-part of U.S. non-provisional application Ser. No. 15/151,579 filed on May 11, 2016 now U.S. Pat. No. 10,426,660 issued on Oct. 1, 2019, and which are incorporated herein in their entirety by reference.

COPYRIGHT NOTICE

A portion of the disclosure of this patent contains material that is subject to copyright protection. The copyright owner has no objection to the reproduction by anyone of the patent document or the patent disclosure as it appears in the Patent and Trademark Office patent files or records, but otherwise reserves all copyright rights whatsoever.

BACKGROUND OF THE INVENTION

Field of the Invention

The present invention relates to a bottle holder. In particular, it relates to a device for holding an eyedropper bottle and positioning it for use.

Description of Related Art

The administration of a drop to the eye requires the steadying of the dropper's tip above the eye to get the drop in the eye, but not so close that the tip touches the eye accidentally. It is also desirable to have the drop land roughly in the center of the eye. In instilling eye drops, one hand holds the dropper while the other hand holds the eye open.

The standard eyedropper or squeeze bottle for instilling eye drops is small, easy to operate, and inexpensive to make. However, there is great difficulty in terms of using it to then instill the drop properly without touching the eye or eyelid, or otherwise one ends up making a mess. This is especially true if one is new to using eye drops or does not have a steady hand. There are both disposable devices and reusable devices known in the art for aiding in the administration of eye drops, such as eyedroppers that rest on the nose (which must be adjustable to fit different face spacings), but all suffer from difficulties in use, accuracy issues, and the like.

BRIEF SUMMARY OF THE INVENTION

The present invention relates to the discovery that administration of eye drops is enhanced greatly by mounting the eyedropper bottle on a device which rests on the boney lower orbital ridge and, as such, a device is designed to use the orbital ridge as a support for such administration.

Accordingly, in one embodiment, there is a device for holding a single use or multiuse eyedropper bottle for administering ophthalmic drops from a dispensing tip of the eyedropper bottle to a user's eye, the device having a top and a bottom side comprising:
  a) a rigid base portion;
  b) a bridge attached to one end of the base portion, adapted for resting the device on the orbital ridge below the user's eye such that drops can be directly instilled to the eye of the user;
  c) a bottle stop on the top side of the device adapted to position the eyedropper bottle such that the dispensing tip is positioned with the dispensing tip in spaced relationship and aligned beyond the edge of the bridge and above the user's eye when the device bridge is positioned on the orbital ridge below the user's eye wherein the bridge and bottle stop are designed together to instill drops directly in the eye without the bottle tip touching the eye; and
  d) wherein a bottom side of the device is adapted to position one or more fingers, such that upon placing the one or more fingers on the adapted portion, the bottle can be squeezed between the fingers in the adapted position and another finger on a top side of the device, or two fingers on the opposite hand can squeeze the bottle to dispense the contents of the bottle.

In another embodiment, there is a method of administering eye drops from an eyedropper bottle with a dispensing tip designed to instill eye drops comprising:
  a) selecting a device, the device having a top of a base portion for holding the eyedropper bottle comprising:
    i. the rigid base portion;
    ii. a bridge attached to one end of the base portion, adapted for resting the device on the orbital ridge below the user's eye such that drops can be directly instilled to the eye of the user;
    iii. a bottle stop on the top side of the device adapted to position the eyedropper bottle such that the dispensing tip is positioned with the dispensing tip in spaced relationship and aligned beyond the edge of the bridge and above the user's eye when the device bridge is positioned on the orbital ridge below the user's eye wherein the bridge and bottle stop are designed together to instill drops directly into the eye without the bottle tip touching the eye; and
    iv. wherein a bottom side of the device is adapted to position one or more fingers, such that upon placing the one or more fingers on the adapted portion, the bottle can be squeezed between the fingers in the adapted position and another finger on a top side of the device, or two fingers on the opposite hand can squeeze the bottle to dispense the contents of the bottle; and
  b) resting the bridge of the device on the orbital ridge of the user;
  c) the user tilting their head back; and
  d) squeezing the eye dropper bottle such that the drops are administered directly into the user's eye.

DETAILED DESCRIPTION OF THE INVENTION

Figure 1:
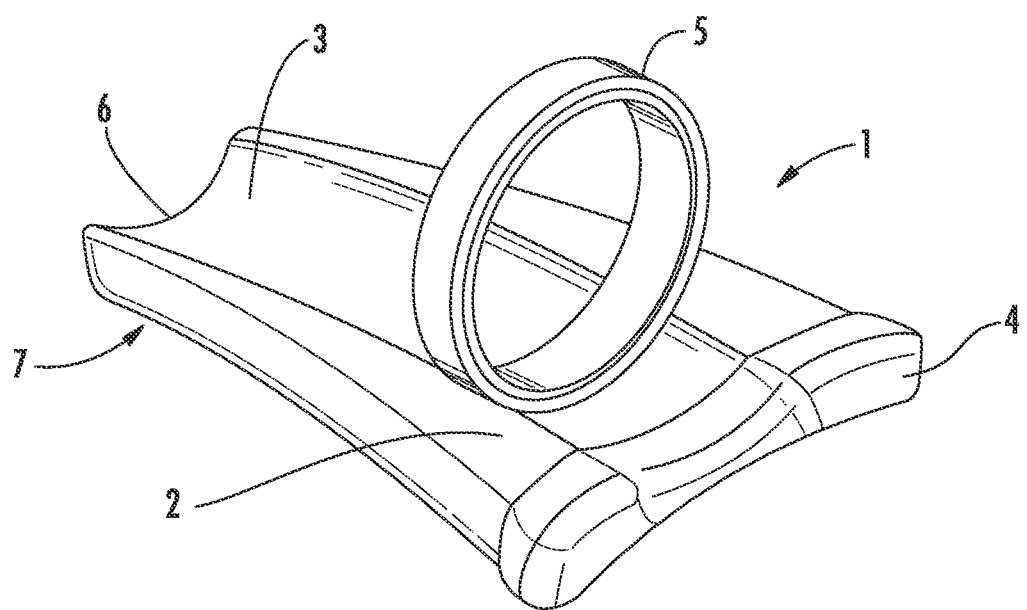
FIG. 1 is a perspective view of a device of the present invention.

While this invention is susceptible to embodiment in many different forms, there is shown in the drawings, and will herein be described in detail, specific embodiments with the understanding that the present disclosure of such embodiments is to be considered as an example of the principles and not intended to limit the invention to the specific embodiments shown and described. In the description below, like reference numerals are used to describe the same, similar, or corresponding parts in the several views of the drawings. This detailed description defines the meaning of the terms used herein and specifically describes embodiments in order for those skilled in the art to practice the invention.

DEFINITIONS

The terms "about" and "essentially" mean±10 percent.

The terms "a" or "an", as used herein, are defined as one or as more than one. The term "plurality", as used herein, is defined as two or as more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

The term "comprising" is not intended to limit inventions to only claiming the present invention with such comprising language. Any invention using the term comprising could be separated into one or more claims using "consisting" or "consisting of" claim language and is so intended.

Reference throughout this document to "one embodiment", "certain embodiments", "an embodiment", or similar terms means that a particular feature, structure, or characteristic described in connection with the embodiment is included in at least one embodiment of the present invention. Thus, the appearances of such phrases in various places throughout this specification are not necessarily all referring to the same embodiment. Furthermore, the particular features, structures, or characteristics may be combined in any suitable manner in one or more embodiments without limitation.

The term "or", as used herein, is to be interpreted as an inclusive or meaning any one or any combination. Therefore, "A, B, or C" means any of the following: "A; B; C; A and B; A and C; B and C; A, B, and C". An exception to this definition will occur only when a combination of elements, functions, steps, or acts are in some way inherently mutually exclusive.

The drawings featured in the figures are for the purpose of illustrating certain convenient embodiments of the present invention and are not to be considered as limitation thereto. The term "means" preceding a present participle of an operation indicates a desired function for which there is one or more embodiments, i.e., one or more methods, devices, or apparatuses for achieving the desired function and that one skilled in the art could select from these or their equivalent in view of the disclosure herein, and use of the term "means" is not intended to be limiting.

As used herein, the term "eye dropper bottle" refers to a bottle, vial, or container holding an ophthalmic solution to be applied to a user's eye.

As used herein, the term "device for holding a single use or multiuse eyedropper bottle" refers to a device for administration of an ophthalmic solution, adapted to position and aide in keeping steady a bottle of ophthalmic solution, for instilling one or more drops into the user's eye. It comprises adaptation to hold the dispensing tip of the bottle over the eye, and adaptation to hold the device steady by providing a bridge which rests on the lower orbital ridge of the eye to which drops are being instilled. The bottle can be squeezed by applying pressure on one side of the bottle, against the base of the device, or just squeezing the bottle between the fingers.

As used herein, the term "administering ophthalmic drops" refers to instilling one or more drops of an ophthalmic solution into the eye of a user from a single use or multiuse eyedropper bottle.

As used herein, the term "user" and "user's eye" refers to a human patient to which it is necessary to instill one or more drops into one or more eyes from a multiuse eyedropper bottle, either applied by the patient or a third party.

As used herein, the term "rigid base" refers to a stiff material, such as a stiff plastic, metal, or the like, of a generally rectangular or oval shape or the like adapted to receive an ophthalmic bottle on its top side and, optionally, the bottom side being adapted to receive a finger of the user. It also has a bridge portion on one end and, optionally, the other end is curved toward the bottom side. In one embodiment, the width is about 1 to 3 inches and the length about 3 to 5 inches.

As used herein, the term "bridge" refers to one end of the base portion adapted to fit on the orbital ridge of a user. Accordingly, it does not need to be wider than an inch or two. It can be straight, but in one embodiment, the base and bridge are curved to match the curve of the human orbital ridge.

As used herein, the term "bottle stop" refers to an adaptation to hold the bottle or position the bottle or stop it from falling into the user's eye during use. In one embodiment, it is a ring or semi-circle, a clip or a V-shaped stop for holding the bottle steady in position. In another embodiment, it may also hold the body of the bottle to secure its position on top.

As used herein, the term "adapted to receive a finger" refers to the base on its bottom side, shaped to have a device like a ring or a semi-circle for holding the finger in place or at least positioning a finger on the bottom side of the base.

As used herein, the term "channel" refers to a groove or indentation on the top side of the base adapted to receive the curvature of an ophthalmic bottle, in order to cradle it as an aid to keep it from moving on the top of the base.

As used herein, the term "curved toward the bottom" refers to an arc built into the base, as shown in the figures, to aide in the gripping of the device and ophthalmic bottle during use. The curve is about 10 degrees to about 25 degrees off of horizontal.

As used herein, the term "squeeze the bottle against the base" refers to pushing a finger on the bottle such that the bottle pushes against the base, which in turn squeezes the bottle to administer one or more drops.

Figure 6:
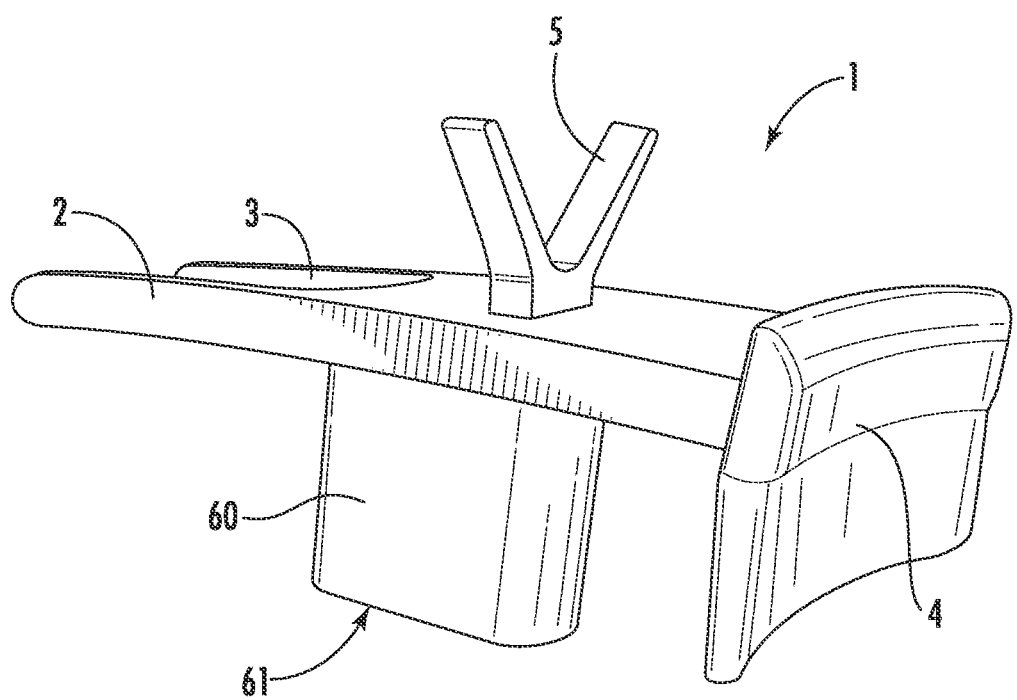
FIG. 6 is a perspective view showing the V-shaped bottle stop portion and a flat bottom with a rectangular shape of the present invention.

As used herein, the term "raised elongated portion" refers to a generally rectangular portion projecting downward from the bottom instead of a thumb ring. In one embodiment, the raised and elongated portion is a flat bottom such as shown in FIG. 6.

DRAWINGS

Now referring to the drawings, FIG. 1 is an embodiment of the present invention, dropper bottle holder 1. The holder device 1 consists of base 2, having channel 3 on a top side of the bottle holder 1 for placement of a dropper bottle (not shown for clarity). At one end of the base 2 there is an orbital ridge bridge 4 for placement of the device vertically on the lower boney orbital ridge of a user. For extra stability, a bottle stop 5 is shown in this embodiment. The bottle stop 5 is a ring, as shown, but could be a partial ring or V-shaped.

The end opposite the orbital ridge bridge 4 is end 6 which is curved downward i.e. the bottom side 7 moving down.

Figure 2:
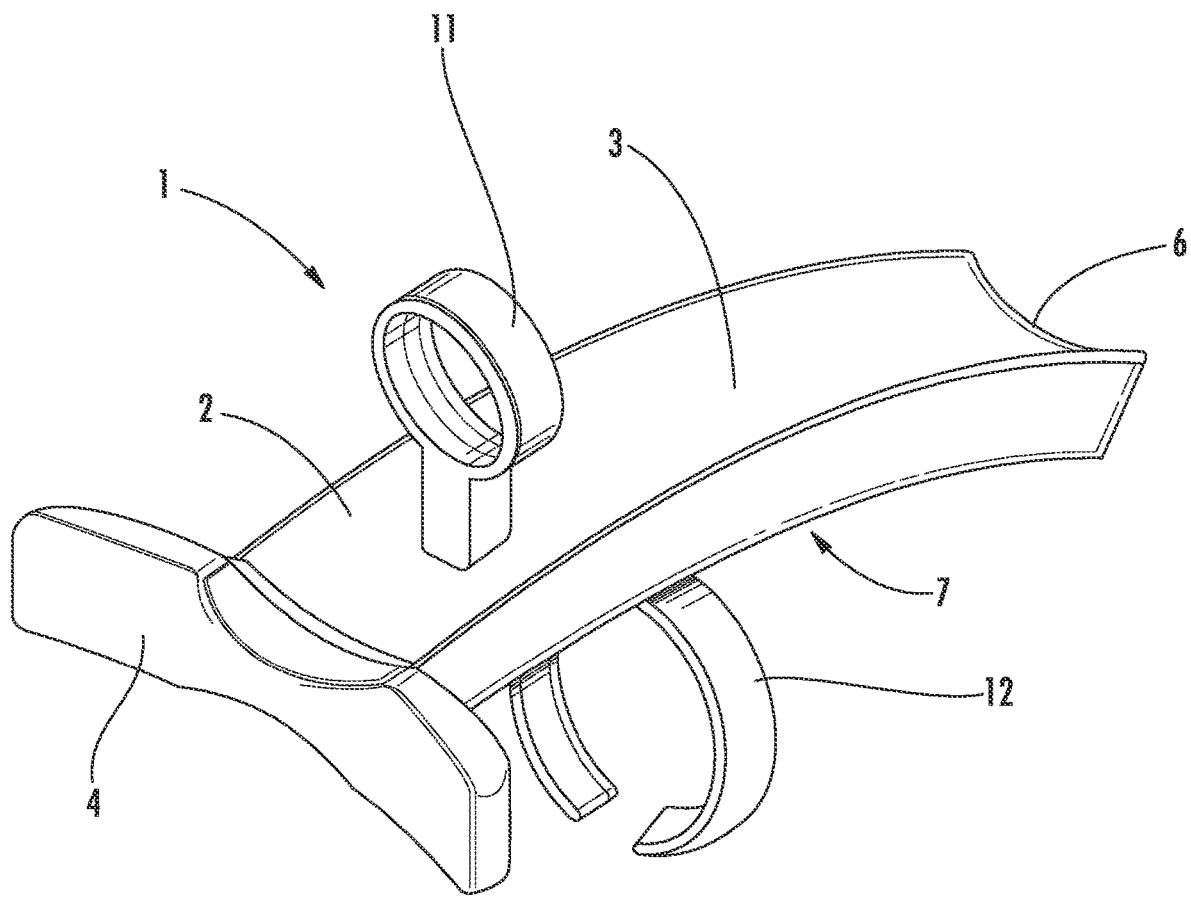
FIG. 2 is a perspective view of a device of the present invention with a finger hold.

FIG. 2 shows another embodiment of device 1 wherein there is a different kind of bottle stop 11 and a finger ring 12 on the bottom side 7 for placement of a finger or a thumb to aide in holding the device 1 and any dropper bottle.

Figure 3:
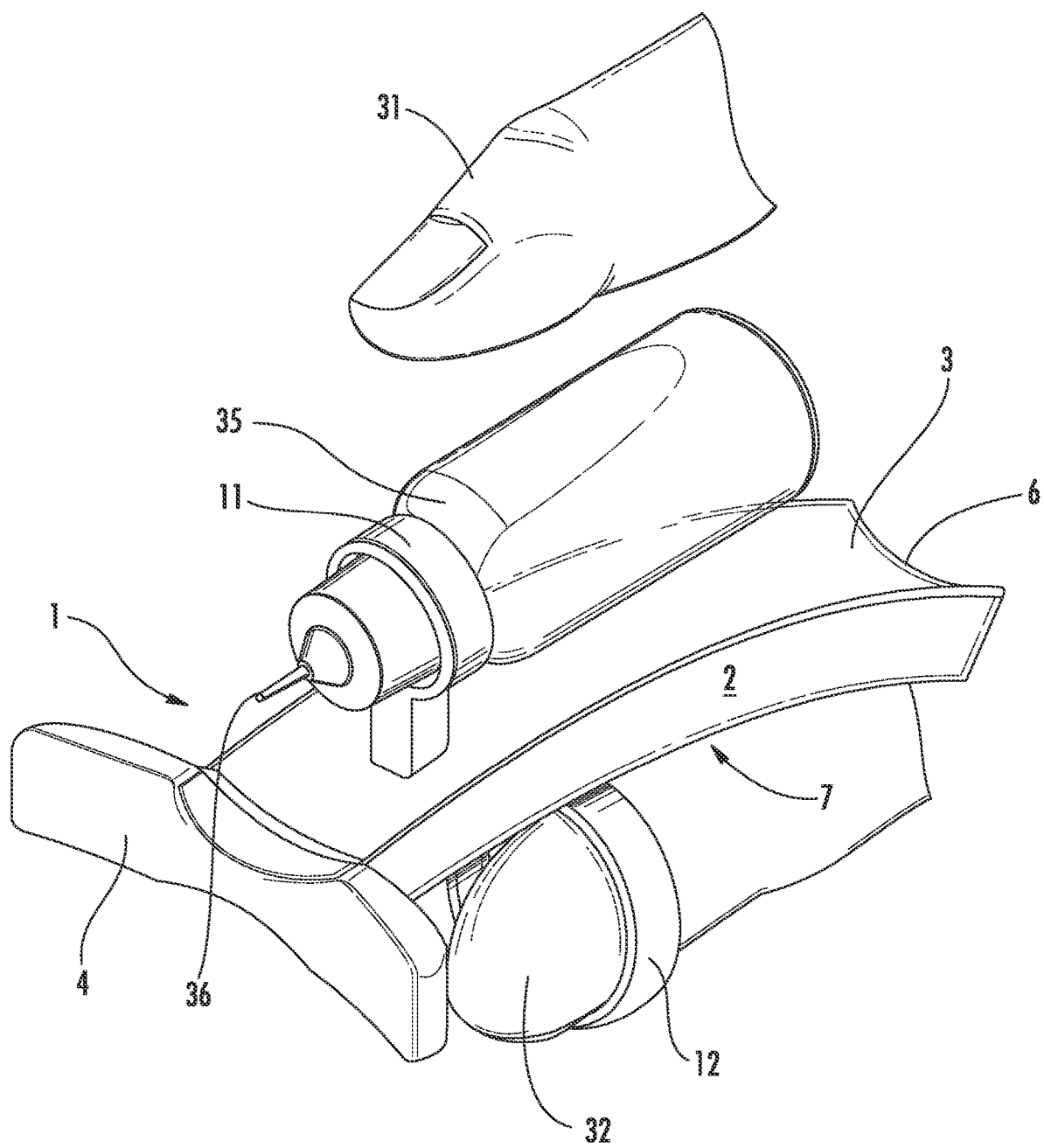
FIG. 3 is a perspective view of a device of the present invention with a bottle mounted.

FIG. 3 shows a user's fingers 31 and 32 on the base 2 and bottom sides 7. Dropper bottle 35 is shown positioned in bottle stop 11 to hold it in place. Fingers 31 and 32 are positioned to squeeze dropper bottle 35 for dispensing of one or more drops from bottle at bottle dispensing tip 36. The finger 32 is positioned in finger ring 12 so that finger 31 placed on dropper bottle 35 can squeeze together from opposing sides of base 2.

Figure 4:
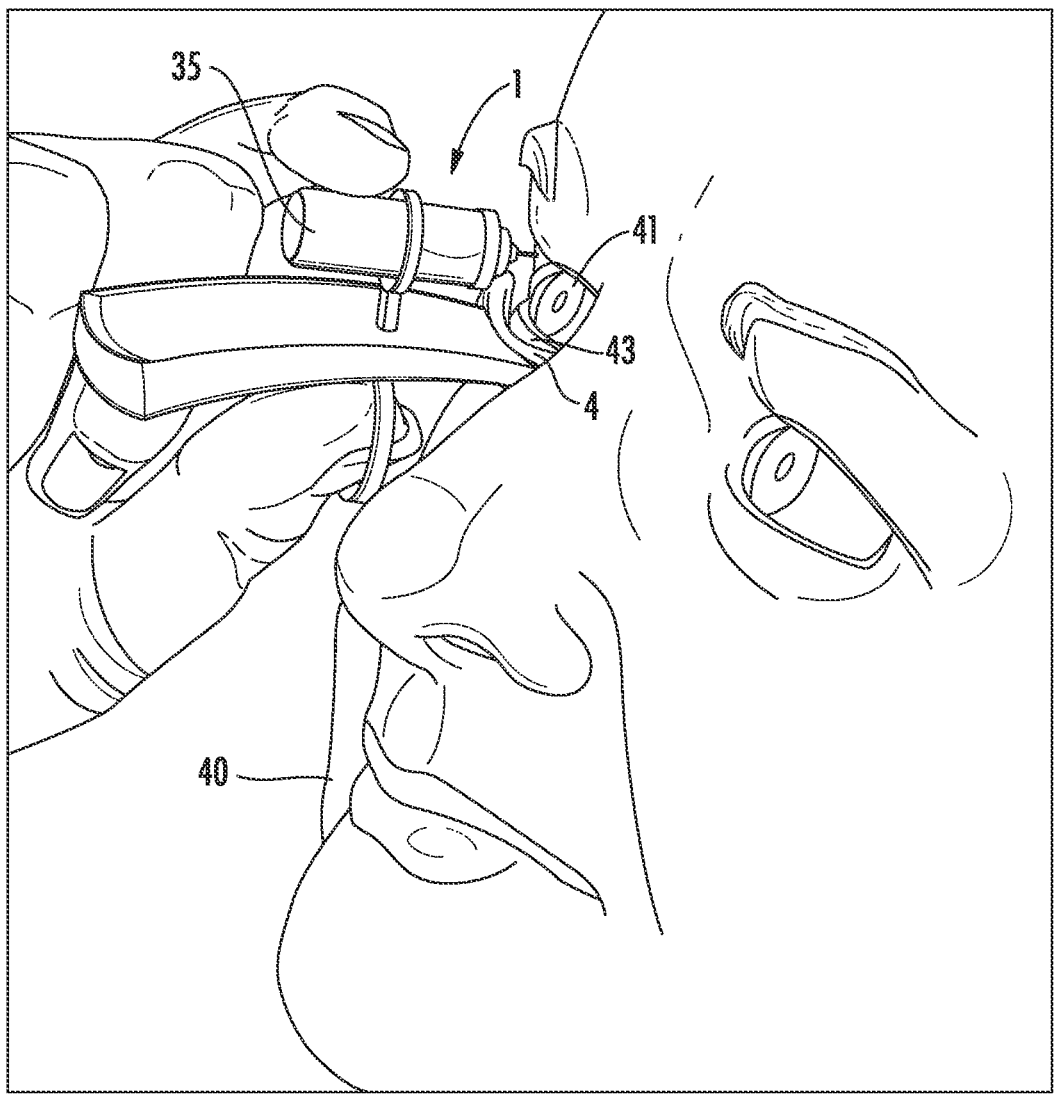
FIG. 4 is a perspective view of the device of the present invention in use.

FIG. 4 shows the device 1 being used with a dropper bottle 35 by user 40 to instill a drop from bottle dispensing tip 36 into user's eye 41. The orbital ridge bridge 4 is seen resting on the user's lower orbital ridge 43 for aligning dispensing tip 36 directly over user's eye 41.

In use, then a user places a dropper bottle in the channel positioned at the bottle stop with the cap off the dispensing tip. The user positions the bridge on the lower orbital ridge with the dispensing tip positioned over the user's eye and dispenses one or more drops by squeezing the bottle on either side, or between the base and the fingers, as shown in FIG. 3. No adjustment is needed for the device, just positioning.

Figure 5:
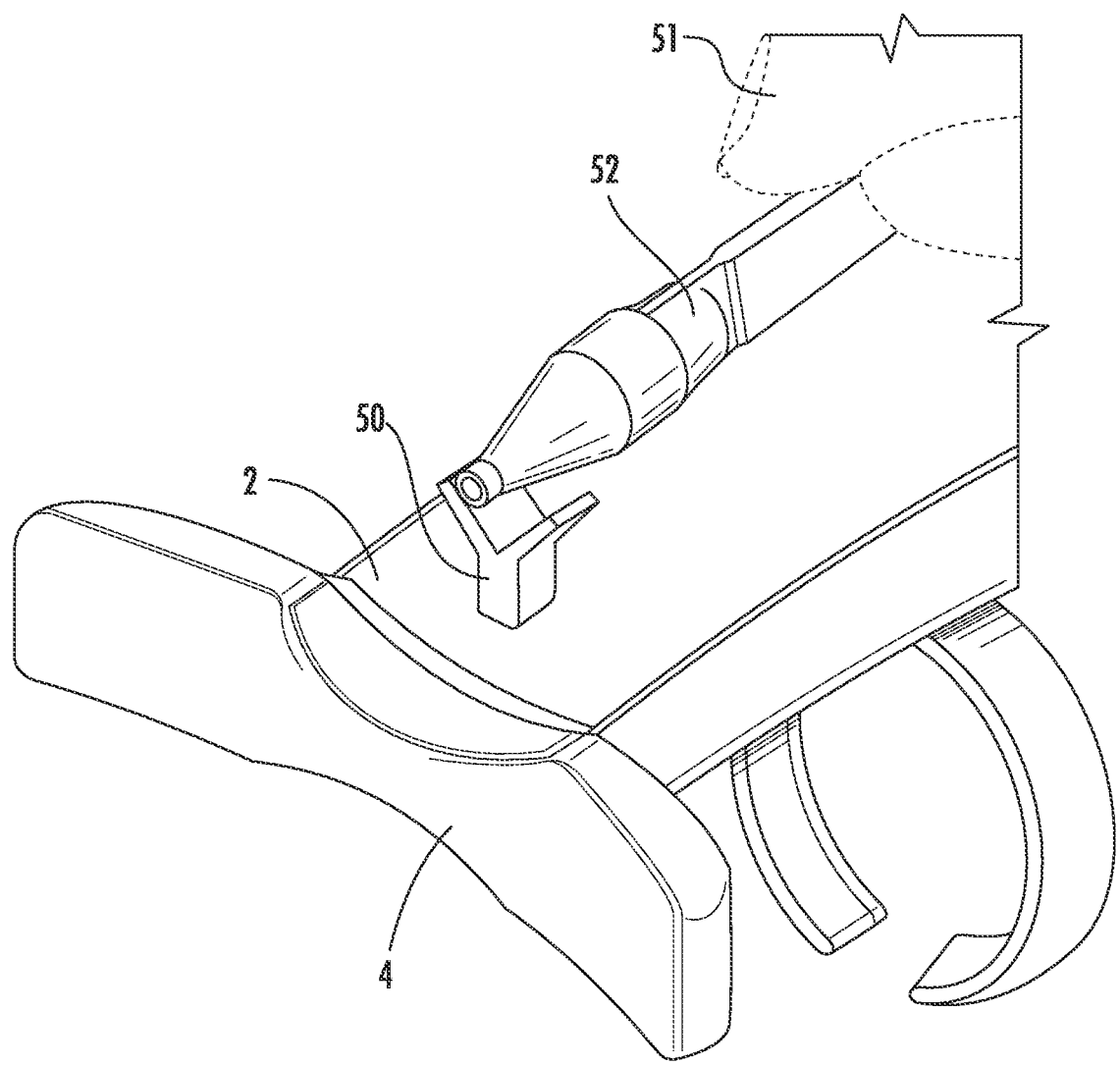
FIG. 5 is a perspective view of a different embodiment of the device of the present invention.

FIG. 5 is an alternate embodiment of the present invention wherein the bottle stop 50 is a V-shaped stop. In this view, user 51 is placing single use dropper bottle 52 into V-shaped stop 50.

FIG. 6 is an embodiment of the device 1 having a V-shaped bottle stop 5. The bottom device 60 has flat bottom 61 with a rectangular shape for two fingers of one hand to hold between them while the device is positioned against the outer orbital ridge while the opposite hand squeezes the bottle. This embodiment is primarily for use with two hands.

Those skilled in the art to which the present invention pertains may make modifications resulting in other embodiments employing principles of the present invention without departing from its spirit or characteristics, particularly upon considering the foregoing teachings. Accordingly, the described embodiments are to be considered in all respects only as illustrative, and not restrictive, and the scope of the present invention is, therefore, indicated by the appended claims rather than by the foregoing description or drawings. Consequently, while the present invention has been described with reference to particular embodiments, modifications of structure, sequence, materials, and the like apparent to those skilled in the art still fall within the scope of the invention as claimed by the applicant.

What is claimed is:

1. A device for holding a single use or multiuse eyedropper bottle for administering ophthalmic drops from a dispensing tip of the eyedropper bottle to a user's eye, the device having a top and a bottom side comprising:
   a) a rigid base portion;
   b) a bridge attached to one end of the base portion, adapted for resting the device on the orbital ridge below the user's eye such that drops can be directly instilled to the eye of the user;
   c) a bottle stop on the top side of the device adapted to position the eyedropper bottle such that the dispensing tip is positioned with the dispensing tip in spaced relationship and aligned beyond the edge of the bridge and above the user's eye when the device bridge is positioned on the orbital ridge below the user's eye wherein the bridge and bottle stop are designed together to instill drops directly in the eye without the bottle tip touching the eye; and
   d) wherein the bottom side of the device is adapted to position two or more fingers, such that upon placing the two or more fingers in the adapted position, the bottle can be squeezed between the fingers in the adapted position and another finger on the top side of the device, or two fingers on the opposite hand can squeeze the bottle to dispense the contents of the bottle.

2. A device according to claim 1 wherein the adaptation on the bottom side of the device is a raised, elongated portion.

3. The device according to claim 1 wherein the end opposite the bridge is curved toward the bottom side.

4. A method of administering eye drops from an eyedropper bottle with a dispensing tip designed to instill eye drops comprising:
   a) selecting a device, the device having a top and a bottom side, comprising:
      i. a rigid base portion;
      ii. a bridge attached to one end of the base portion, adapted for resting the device on the orbital ridge below the user's eye such that drops can be directly instilled to the eye of the user;
      iii. a bottle stop on the top side of the device adapted to position the eyedropper bottle such that the dispensing tip is positioned with the dispensing tip in spaced relationship and aligned beyond the edge of the bridge and above the user's eye when the device bridge is positioned on the orbital ridge below the user's eye wherein the bridge and bottle stop are designed together to instill drops directly into the eye without the bottle tip touching the eye; and
      iv. wherein the bottom side of the device is adapted to position two or more fingers, such that upon placing the two or more fingers in the adapted position, the bottle can be squeezed between the fingers in the adapted position and another finger on the top side of the device, or two fingers on the opposite hand can squeeze the bottle to dispense the contents of the bottle;
   b) resting the bridge of the device on the orbital ridge of the user;
   c) the user tilting their head back; and
   d) squeezing the eye dropper bottle such that the drops are administered directly into the user's eye.

* * * * *